(12) United States Patent
Grosser et al.

(10) Patent No.: US 7,689,370 B2
(45) Date of Patent: Mar. 30, 2010

(54) ON-LINE ABSOLUTE VISCOSITY MEASUREMENT SYSTEM

(75) Inventors: Richard W. Grosser, Long Beach Township, NJ (US); Eugenio Sanchez, Pitman, NJ (US); Angela Galiano-Roth, Mullica Hill, NJ (US); Alan M. Schilowitz, Highland Park, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 12/009,235

(22) Filed: Jan. 17, 2008

(65) Prior Publication Data

US 2008/0228424 A1 Sep. 18, 2008

Related U.S. Application Data

(60) Provisional application No. 60/881,421, filed on Jan. 19, 2007.

(51) Int. Cl.
*G01N 11/00* (2006.01)
*G01K 17/00* (2006.01)
*G01F 1/00* (2006.01)

(52) U.S. Cl. .......................... 702/50; 73/32 A; 702/45; 702/100; 702/136

(58) Field of Classification Search .................. 702/42, 702/50, 55, 99, 100, 130, 136; 73/32 A, 73/53.05; 208/18; 252/71
See application file for complete search history.

(56) References Cited

U.S. PATENT DOCUMENTS

| 4,674,322 | A * | 6/1987 | Stangeland ................ 73/32 A |
| 6,546,785 | B1 * | 4/2003 | Discenzo ................... 73/53.05 |
| 2004/0119046 | A1 * | 6/2004 | Carey et al. ................... 252/71 |
| 2004/0154957 | A1 * | 8/2004 | Keeney et al. ................ 208/18 |

* cited by examiner

*Primary Examiner*—John H Le
(74) *Attorney, Agent, or Firm*—Gary P. Katz (57) ABSTRACT

The present invention provides systems and methods for determining the viscosity of a lubricating fluid in a process on line. The method of the present invention obviates the need to accurately control the temperature of the lubricating fluid in the system when taking fluid viscosity measurements.

22 Claims, 5 Drawing Sheets

ON-LINE ABSOLUTE VISCOSITY MEASUREMENT SYSTEM

This application claims priority of Provisional Application 60/881,421 filed Jan. 19, 2007.

TECHNOLOGY FIELD

The present invention relates to the field of systems and methods of determining fluid viscosity in industrial processes.

BACKGROUND

For years, the measurement of oil viscosity in a lubricating system has been relegated to an intermittent and static off-line determination. There has been a long felt need for a means of monitoring the viscosity of lubricating fluids real time and on-line. There are commercially available viscometers, but it is difficult to achieve consistent and accurate on-line viscosity measurements using these viscometers. Many of the commercially available viscometers are not well suited for on-line process control, because they are very sensitive to contaminants and temperature gradients in both the lubricating fluids and the viscometer itself. In a process environment, it is very difficult to maintain lubricating fluids free of contaminants and to accurately control the temperature of the lubricating fluid to a fixed temperature.

With conventional methods and systems for measuring viscosity, temperature control is crucial to achieving accurate results. The significance of temperature control for achieving accurate viscosity measurements with conventional viscometers has been confirmed by laboratory experiments. For example, for a sample of lubricating fluid held in a constant temperature bath for an extended period of time, the measured viscosity of the sample of lubricating fluid can change 5%-10% due to effective temperature fluctuations at the measurement point even without significant change in the bulk temperature of the sample of lubricating fluid. Consistent viscosity measurements can only be achieved if the sample of lubricating fluid, the sensor head of the viscometer, and the sensor stem of viscometer are held at the same constant temperature.

The problem of temperature control is further complicated if viscosity is estimated by combining data from several pieces of equipment spread across a system, rather than being measured directly with a viscometer. Most commonly, viscosity is estimated by measuring flow across a measured pressure differential and using the Hagen-Poiseuille equation to determine viscosity. As noted above, this type of method of estimating viscosity further complicates the problem of temperature control. The temperature of the lubricating fluid usually needs to be controlled at all the measurement points (e.g., at the locations of any flowmeters and pressure sensors). Such temperature control can be very difficult, particularly, if the measurement points are located in different parts of a process system having different operating temperatures. Variations in the temperatures at the various measurement points can also vary depending on a number of conditions, such as time of day, season, equipment status, and the like.

Figure 1:
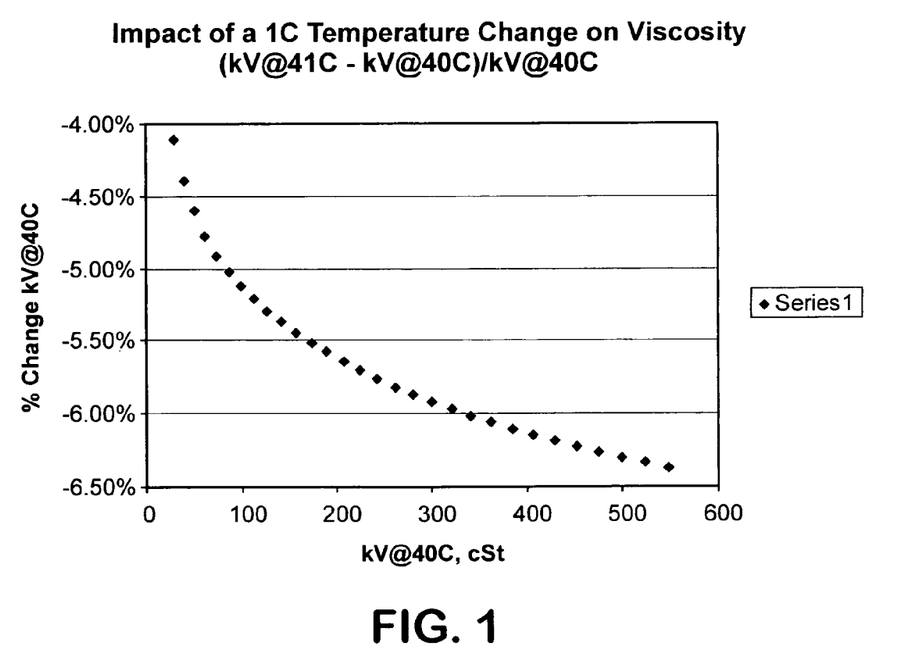
FIG. 1 depicts a graph of a data simulation quantitatively demonstrating the magnitude of the impact that temperature has on viscosity measurement for a fluid with a viscosity index of 95.

A data simulation, as illustrated by FIG. 1, quantitatively demonstrates the magnitude of the impact that temperature has on viscosity measurement: for this particular fluid, a change as small as one degree Celsius can change viscosity by about 4%-7%. As shown in FIG. 1, for an ISO 220 industrial lubricant oil, the kinematic viscosity measured in centistokes at 40 degrees Celsius ("cSt @ 40° C.") is about 5.7% higher than at 41° C. This difference does not even account for any random noise error that may be contained in the viscosity measurement. To achieve viscosity measurement biases lower than 5% with conventional methods and systems, it may be necessary to accurately control measurement temperatures to within 1° C., or better. The sensitivity of viscosity to temperature depends on the type and composition of fluid being tested.

In light of problems with prior-art methods and systems of determining viscosity on-line, there is a need for systems and methods of determining viscosity on-line that compensate for temperature differences in the system. Accordingly, this invention satisfies that need.

SUMMARY

One embodiment of the present invention provides on-line methods for estimating the kinematic viscosity ($kV_{standard}$) of a lubricating fluid at a standard temperature ($T_{standard}$). Here, standard temperature ($T_{standard}$) refers to a specified temperature used to compare the properties of fluids in a standardized manner. For example, it is common to report the kinematic viscosity of industrial lubricants at standard temperatures such as 40.0° C. or 100.0° C.

The present invention provides an on-line method for estimating kinematic viscosity ($kV_{standard}$) of a fluid at a standard temperature ($T_{standard}$) including the steps of: determining the absolute viscosity (aV) of the fluid at a section A in the system; measuring a property of the fluid (P); determining a virtual temperature ($T_V$) of the fluid using the measured property of the fluid (P); estimating the kinematic viscosity (kV) of the fluid from the absolute viscosity (aV) of the fluid; and extrapolating the kinematic viscosity ($kV_{standard}$) of the fluid at a standard temperature ($T_{standard}$) using the kinematic viscosity (kV) of the fluid and the virtual temperature ($T_V$) of the fluid. The virtual temperature ($T_V$) of the fluid refers to an effective fluid temperature that is consistent with measured properties of the fluid—such as viscosity, pressure, flowrate, and temperature measured at multiple points. The virtual temperature ($T_V$) of the fluid is often different than any actually measured temperature, because it accounts for differences in temperature measurements across a section of the system.

The present invention also provides an on-line method for estimating kinematic viscosity ($kV_{standard}$) of a fluid at a standard temperature ($T_{standard}$) including the steps of: determining the absolute viscosity (aV) of the fluid at a section A in the system; measuring at least two properties ($P_N$) of the fluid at different points in the system; determining the virtual temperature ($T_V$) of the fluid at section A using the measured at least two properties ($P_N$) of the fluid with a relationship that correlates the at least two properties ($P_N$) of the fluid with the virtual temperature ($T_V$) of the fluid at section A; estimating the kinematic viscosity (kV) of the fluid from the absolute viscosity (aV) of the fluid; and extrapolating the kinematic viscosity ($kV_{standard}$) of the fluid at a standard temperature ($T_{standard}$) using the kinematic viscosity (kV) of the fluid and the virtual temperature ($T_V$) of the fluid.

The present invention also provides methods for determining the absolute viscosity (aV) of the fluid at a section A in the system by measuring the flow rate (F) of the lubricating fluid across a measured pressure differential ($P_1$-$P_2$) and solving an appropriate viscosity estimation equation, such as, for example, the Hagen-Poiseuille equation. Here, section A refers to the section of the system that encompasses the points at which the properties of the fluid are measured to estimate the absolute viscosity (aV) of the fluid. For example, when the Hagen-Poiseuille equation is used to estimate the absolute viscosity (aV) of the fluid, section A includes a first location where pressure ($P_1$) is measured, a second location where pressure ($P_2$) is measured, and a third location where flow rate (F) is measured.

The present invention also provides methods for determining the virtual temperature ($T_V$) of the fluid including the steps of: characterizing an equation that correlates the temperature (T) and a property of the fluid (P) under controlled laboratory conditions; taking at least three measurements ($P_n$) of said property of the fluid in the system; using the characterized equation correlating the temperature (T) and said property of the fluid (P) to estimate virtual temperature values ($T_{Vn}$) of the fluid at section A corresponding to the measurements ($P_n$) of said property of the fluid; characterizing an equation that correlates the at least three property measurements ($P_n$) of the fluid and their corresponding virtual temperature values ($T_{Vn}$); and determining the virtual temperature ($T_{Vn}$) of the fluid at section A of the system using a measurement of said property ($P_n$) of the fluid and the characterized equation that correlates said property ($P_n$) of the fluid and the virtual temperature ($T_{Vn}$).

The present invention also provides methods for estimating the kinematic viscosity (kV) including the steps of: estimating the density (D) of the fluid at section A using the virtual temperature ($T_V$) of the fluid at section A and a relationship that correlates the temperature (T) of the fluid with the density (D) of the fluid; and determining kinematic viscosity (kV) using the absolute viscosity (aV) of the fluid, the density (D) of the fluid, and a relationship that correlates the absolute viscosity (aV) and density (D) of the fluid to the kinematic viscosity (kV).

The general description and the following detailed description are exemplary and explanatory only and are not restrictive of the invention, as defined in the appended claims. Other aspects of the present invention will be apparent to those skilled in the art in view of the detailed description of the invention as provided herein.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale.

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, references to values stated in ranges include each and every value within that range.

The present invention provides systems and methods for determining the viscosity of a lubricating fluid in a process on line. The method of the present invention obviates the need to accurately control the temperature of the lubricating fluid in the system when taking fluid viscosity measurements.

System for Determining the Viscosity of a Fluid On-Line

Figure 2:
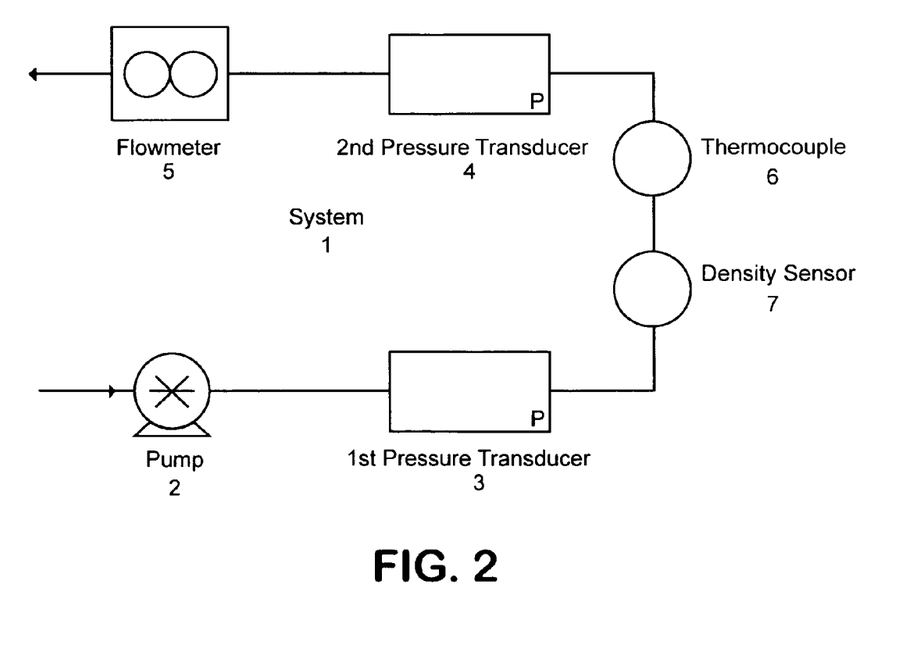
FIG. 2 depicts a block diagram of an exemplary system according to the present invention.

Referring to FIG. 2, there is provided an embodiment of the system 1 of the present invention that can be used for measuring various properties of the fluid in the system 1. The viscosity of the fluid may be derived using methods as provided herein. In one embodiment, the system 1 may comprise a pump 2, a first pressure transducer 3, a second pressure transducer 4, a flowmeter 5, a thermocouple 6, and a density sensor 7. The flowmeter 5 is preferably a positive displacement flowmeter, and the thermocouple 6 is preferably an isothermal thermocouple. The pump 2 and the pressure transducers 3, 4 can be any conventional types. As shown in FIG. 2, the system 1 may employ a pump 2, a first pressure transducer 3 located downstream of the pump 1, a second pressure transducer 4 located downstream of the first pressure transducer 3, a flowmeter 5 located downstream of the second pressure transducer 4, and a thermocouple 6 and density sensor 7 preferably located downstream of the first pressure transducer 3 and upstream of the second pressure transducer 4. Additionally, the system 1 may include one or more sensors to determine whether the flow of the fluid through the system 1 is laminar.

Method for Determining the Viscosity of a Fluid On-Line

According to another aspect of the invention, provided is a real-time, on-line method of monitoring the kinematic viscosity ($kV_{standard}$) of a fluid in the system 1 at a standard temperature ($T_{standard}$). According to one method, monitoring the kinematic viscosity ($kV_{standard}$) of a fluid comprises characterizing the properties of the fluid, calibrating the system 1 using the characterized fluid, and determining the kinematic viscosity ($kV_{standard}$) of the fluid in real time as it continually degrades in the system 1.

Characterizing the Properties of the Fluid

In one embodiment, the fluid is preferably tested under laboratory conditions and kinematic viscosity ($kV_n$) and density ($D_n$) measurements are taken at a minimum of two temperatures ($T_n$) using ASTM methods. Then, the kinematic viscosity and density properties of the fluid can be correlated to temperature by using the kinematic viscosity ($kV_n$), density ($D_n$), and temperature ($T_n$) measurements to calculate the coefficients for equations that correlate kinematic viscosity and temperature, or density and temperature.

The kinematic viscosity (kV) of the fluid can be correlated to the temperature (T) of the fluid by calculating the coefficients of any mathematical relationship that correlates the kinematic viscosity ($kV_n$) and temperature ($T_n$) measurements of the fluid. Preferably, the kinematic viscosity (kV) of the fluid is correlated to the temperature (T) of the fluid by calculating the coefficients A and B of the Walther-MacCaull equation. (Walther, C., "The Variation of Viscosity with Temperature-I, II, III," Erdol und Teer, Vol. 5, 1928, p. 510, 526, 614). The corresponding kinematic viscosity ($kV_n$) and temperature ($T_n$) measurements taken in the laboratory can be used to characterize the fluid by solving the coefficients of the Walther-MacCaull equation.

For example, an ISO 220 oil with kV @ 40° C.=217.2 cSt and kV @ 100° C.=217.2 cSt can be fitted to the Walther-MacCaull Equation:

$$\log_{10}(\log_{10}(kV_n+0.7))=A-B*\log_{10}(T_n)$$

where $kV_n$ is the kinematic viscosity of the oil in centistokes at temperature $T_n$ (in degrees Kelvin), and A and B are the coefficients that characterize the fluid. When the given kinematic viscosity ($kV_n$) and temperature ($T_n$) measurements of the fluid are used to solve for the coefficients of the Walther-MacCaull equation, they yield values for A of about 8.8 and for B of about 3.4. Thus, the Walther-MacCaull Equation characterized for the ISO 220 oil is: $\log_{10}(\log_{10}(kV_n+0.7))=8.8-3.4*\log_{10}(T_n)$.

The density (D) of the fluid can be correlated to the temperature (T) of the fluid by calculating the coefficients of any mathematical relationship that correlates the density ($D_n$) and temperature ($T_n$) measurements of the fluid. For example, a linear relationship—such as $T_n=a+b*D_n$—can be used to correlate the density ($D_n$) of the fluid to temperature ($T_n$) of the fluid, where a and b are constants that characterize the fluid and best fit the density ($D_n$) and temperature ($T_n$) measurements of the fluid.

Calibrating the System

Once the properties of the fluid are measured and characterized, the fluid is circulated through the system 1 to determine the calibration coefficient (C) of the system 1. The fluid is preferably introduced into the system 1 before it has started to degrade to ensure that the actual properties of the fluid are substantially the same as the characterized properties of the fluid.

Once the fluid is circulated through the system 1, the pressure ($P_{1n}$) of the fluid in the system 1 is measured by the first pressure transducer 3 and the pressure ($P_{2n}$) of the fluid further downstream in the system 1 is measured by the second pressure transducer 4. The flow rate ($F_n$) of the fluid in the system 1 is measured by the flowmeter 5 and the temperature ($T_n$) of the fluid in the system 1 is measured by the thermocouple 6. Preferably, the measurements of pressure ($P_{1n}$, $P_{2n}$), flow rate ($F_n$), and temperature ($T_n$) are taken continuously at least ten times per hour for a minimum of 10 days. An average temperature (T), average pressure ($P_1$), average pressure ($P_2$), and average flow rate (F) are calculated for the measurements ($T_n$, $P_{1n}$, $P_{2n}$, $F_n$) taken over the ten day period.

Using the average temperature (T) and the Walther-MacCaull equation already characterized for the fluid with coefficients A and B, a kinematic viscosity (kV) correlated to the average temperature (T) can be calculated. Also, using the average temperature (T) and the density equation already characterized for the fluid with coefficients a and b, a density (D) correlated to the average temperature (T) can be calculated. Then, the calculated kinematic viscosity (kV) and density (D) can be used to calculate the absolute viscosity (aV) corresponding to the average temperature (T). For example, the absolute viscosity (aV) may be estimated by using the known relationship: aV=kV*D, where aV is the absolute viscosity of the fluid, kV is the kinematic viscosity of the fluid, and D is the density of the fluid.

Then, the average pressure ($P_1$), pressure ($P_2$), flow rate (F), and absolute viscosity (aV) can be used to solve the Hagen-Poiseuille equation and determine the calibration coefficient (C). Preferably, the Hagen-Poiseuille equation is represented as: $C=aV*F/(P_1-P_2)$. The calibration coefficient (C) of the system 1 compensates for temperature differences in the fluid and pipe size and geometry differences at various points in the system 1 that affect the on-line measurement of fluid viscosity.

Determining the Fluid's Viscosity On-line

Using the characterized properties of the fluid and the calibration coefficient (C) of the system 1, the fluid's viscosity can be determined continuously in real time as the fluid degrades in the system 1. One aspect of the present invention provides on-line methods for estimating kinematic viscosity ($kV_{standard}$) of a lubricating fluid at a standard temperature ($T_{standard}$). Here, standard temperature ($T_{standard}$) refers to a specified temperature used to compare the properties of fluids in a standardized manner. For example, it is common to report the kinematic viscosity ($kV_{standard}$) of industrial lubricants at standard temperatures ($T_{standard}$) such as 40.0° C. or 100.0° C.

According to one method, determining the kinematic viscosity ($kV_{standard}$) of the fluid in the system 1 comprises: determining the absolute viscosity (aV) of the fluid at a section A in the system 1; measuring a property of the fluid (P) in the system 1; determining a virtual temperature ($T_V$) of the fluid using the measured property of the fluid (P); estimating the kinematic viscosity (kV) of the fluid from the absolute viscosity (aV) of the fluid; and extrapolating the kinematic viscosity ($kV_{standard}$) of the fluid at a standard temperature ($T_{standard}$) using the kinematic viscosity (kV) of the fluid and the virtual temperature ($T_V$) of the fluid.

Preferably, the absolute viscosity (aV) of the fluid at a section A in the system 1 is determined by measuring the flow rate (F) of the fluid across a measured pressure differential ($P_1-P_2$) and solving an appropriate viscosity estimation equation. Here, section A refers to the section of the system 1 that encompasses the points at which the properties of the fluid are measured to estimate the absolute viscosity (aV) of the fluid. For example, referring to FIG. 2, section A is the section of the system 1 that encompasses the first location where pressure ($P_1$) is measured, the second location where pressure ($P_2$) is measured, and the location where flow rate (F) is measured. The viscosity estimation equation may be any equation that correlates observed properties of a fluid with the absolute viscosity (aV) of the fluid, but is preferably the Hagen-Poiseuille equation.

For example, the Hagen-Poiseuille equation may be represented as: $aV=(P_1-P_2)*C/F$; where aV is the absolute viscosity of the fluid, $P_1$ is the pressure of the fluid at a first location in the system 1, $P_2$ is the pressure of the fluid at a second location in the system 1 downstream from the first location, C is the calibration coefficient of the system 1, and F is the flow rate of the fluid through the system 1. Thus, the absolute viscosity (aV) of the fluid may be determined by solving the Hagen-Poiseuille equation—$aV=(P_1-P_2)*C/F$—with the pressure measurement (P1) measured by the first pressure transducer 3, the pressure measurement (P2) measured by the second pressure transducer 4, the flow rate measurement (F) measured by the flowmeter 5, and the calibration coefficient (C) determined for the system 1. Preferably, absolute viscosity determinations ($aV_n$) of the fluid in the system 1 are made continuously at least ten times per hour and for at least ten days.

Also, measurements of a property of the fluid ($P_n$) in the system 1 are preferably taken continuously at least ten times per hour and for at least ten days. The property of the fluid (P) can be any property of the fluid that is correlated to the actual temperature of the fluid where the viscosity is measured, including, but not limited to conductivity, impedance, viscosity, and another fluid temperature. Alternatively, the property of the fluid (P) can be any mathematically functional combination of properties of the fluid that are correlated to the actual temperature of the fluid where its viscosity is measured, including, but not limited to conductivity, impedance, viscosity, and another temperature. The property of the fluid (P), however, is preferably another temperature (T) of the fluid in the system 1. Further, the property of the fluid (P) can be measured by one sensor, multiple sensors, or a combination of sensors in the system 1 (shown as thermocouple 6 in FIG. 2). For example, the property of the fluid (P) can be the average of multiple temperature measurements ($T_n$).

In one embodiment, the continuous determinations of absolute viscosity ($aV_n$) and measurements of a fluid property ($P_n$) (e.g. temperature ($T_n$)) may be used to determine the virtual temperature ($T_{Vn}$) of the fluid in the system 1. The virtual temperature ($T_V$) of the fluid refers to an effective temperature of the fluid where its viscosity is being measured that is consistent with measured properties of the fluid—such as viscosity, pressure, flowrate, or another fluid temperature. Often, the virtual temperature ($T_V$) of the fluid is different than any measured temperature (T) of the fluid, because it accounts for differences in fluid temperature measurements ($T_n$) across a section of the system 1.

A virtual temperature ($T_{Vn}$) may be determined by correlating it to a measurement of a property of the fluid ($P_n$) (e.g. temperature ($T_n$)). An equation correlating the virtual temperature ($T_V$) of the fluid to a property of the fluid (P) (e.g. temperature (T)) can be obtained by performing a regression on virtual temperature values ($T_{Vn}$) and fluid property measurements ($P_n$) (e.g. temperature ($T_n$)) in the system 1. A regression can be any analysis of empirical data to determine a functional relationship between two or more correlated variables.

In one embodiment, the virtual temperature values ($T_{Vn}$) of the regression are determined by correlating the continuous determinations of absolute viscosity ($aV_n$) of the fluid to virtual temperature values ($T_{Vn}$) of the fluid using the density and kinematic viscosity equations characterized for the fluid. First, for example, density values ($D_n$) corresponding to the continuously measured fluid property ($P_n$) (e.g. temperature ($T_n$)) may be determined using the density equation characterized for the fluid (e.g. $T_n=a+b*D$). Then, using these density values ($D_n$) and the known relationship: $kV_n=aV_n/D_n$, the absolute viscosity measurements ($aV_n$) of the fluid can be correlated to corresponding kinematic viscosity values ($kV_n$). For each determined kinematic viscosity value ($kV_n$) corresponding to the continuous absolute viscosity determinations ($aV_n$) and fluid property measurements ($P_n$) (e.g. temperature ($T_n$)) a virtual temperature value ($T_{Vn}$) is calculated using the kinematic viscosity equation (e.g. Walther-MacCaull equation) characterized for the fluid. Thus, the virtual temperature values ($T_{Vn}$) for the regression of virtual temperature ($T_V$) of the fluid on a property of the fluid (P) (e.g. temperature (T)) can be determined.

Once the continuous measurements of the property of the fluid ($P_n$) (e.g. temperature ($T_n$)) and corresponding virtual temperature values ($T_{Vn}$) of the fluid are collected, a regression may be performed on the data set to determine a relationship that correlates the fluid property measurements ($P_n$) (e.g. temperature ($T_n$)) to the virtual temperature values ($T_{Vn}$). The relationship that correlates the empirical data points ($P_n$) and ($T_{Vn}$) can be any conventional mathematical relationship. For example, a linear relationship—such as $T_{Vn}=a+b*P_n$, where a and b are constants that best fit the empirical data points ($P_n$) and ($T_{Vn}$)—can be used to correlate the property of the fluid (P) (e.g. temperature (T)) and the virtual temperature of the fluid ($T_V$).

According to one embodiment, after the fluid has been flowing through the system 1 and the absolute viscosity determinations ($aV_n$) and fluid property measurements ($P_n$) (e.g. temperature ($T_n$)) have been made continuously at least 10 times per hour for at least ten days, an on-line determination of the kinematic viscosity ($kV_{standard}$) of the fluid at a standard temperature ($T_{standard}$) may be made.

A given determination of the fluid's absolute viscosity ($aV_n$) and a corresponding measurement of fluid property ($P_n$) (e.g. temperature ($T_n$)) can be used to determine the kinematic viscosity ($kV_n$) of the fluid. For example, a density value ($D_n$) corresponding to the fluid property ($P_n$) (e.g. temperature ($T_n$)) may be determined using the density equation already characterized for the fluid (e.g. $T_n=a+b*D_n$). Then, using this density value ($D_n$) and the known relationship: $kV_n=aV_n/D_n$, the absolute viscosity determination ($aV_n$) of the fluid can be correlated to a corresponding kinematic viscosity value ($kV_n$).

Once a kinematic viscosity ($kV_n$) of the fluid is determined, it may be extrapolated to a kinematic viscosity ($kV_{standard}$) of the fluid at a standard temperature ($T_{standard}$) by preferably using a virtual temperature ($T_{Vn}$) of the fluid and the well-known Walther-MacCaull Equation. A virtual temperature ($T_{Vn}$) corresponding to the fluid property ($P_n$) (e.g. temperature ($T_n$)) may be determined using the virtual temperature equation already characterized for the fluid (e.g. $T_{Vn}=a+b*P_n$). Then, the virtual temperature ($T_{Vn}$) may be used with the Walther-MacCaull Equation having already determined coefficients A and B that characterize the fluid (i.e. $\log_{10}(\log_{10}(kV_n+0.7))=A-B*\log_{10}(T_{Vn})$). An on-line kinematic viscosity measurement ($kV_n$) may be extrapolated to a kinematic viscosity ($kV_{standard}$) at a standard temperature ($T_{standard}$) using the Walther-MacCaull equation, as follows:

$$kV_{standard}=10^{(10^{[A*T_{standard}-B]})}-0.7$$

where A and B are the coefficients determined to characterize the fluid. For example, to extrapolate an on-line kinematic viscosity measurement ($kV_n$) to a kinematic viscosity ($kV_{standard}$) at a standard temperature ($T_{standard}$) of 40° C.=313.15 K, the equation is $$kV_{40}=10^{(10^{[A*313.15-B]})}-0.7$$

The kinematic viscosity ($kV_{standard}$) at a fixed standard temperature ($T_{standard}$) (e.g., 40° C.) is typically constant as a function of time if a fluid composition is not changing. If the fluid composition is changing slowly, for small fluid changes (e.g., degradation) the –B (slope) typically does not affect the change detection process. The kinematic viscosity ($kV_{standard}$) at a fixed standard temperature ($T_{standard}$) (e.g., 40° C.) as a function of a given measured pair ($kV_n$, $T_{Vn}$) can be calculated from the Walther Equation, rearranging:

$$\log_{10}(\log_{10}(kV_{standard}+0.7))=\log_{10}(\log_{10}(kV_n+0.7))-B(\log_{10}(T_{actual})-\log_{10}(T_{standard})) \text{ or}$$

$$kV_{standard}=(kV_n+0.7)^{(Tactual/Tstandard)^{\wedge}B}-0.7$$

where $kV_n$ is a kinematic viscosity of the fluid determined on-line, $T_{actual}$ is the fluid temperature at the point where viscosity is measured, and B is a coefficient specific to the fluid as described above.

The Walter-MacCaull equation uses the fluid temperature in the system 1 at the point where the viscosity of the fluid is measured. The temperature at the point of viscosity measurement, however, can be difficult to measure. Further, in the system 1 exemplified in FIG. 2, the viscosity is not actually measured, rather it is approximated with the Hagen-Poiseuille equation using various other measured fluid properties (e.g., flow, pressure, and the like.) at different points in the system 1. In the embodiment of FIG. 2, there is no actual point of viscosity measurement at which a temperature can be measured. According to the present invention, the virtual temperature ($T_{Vn}$) of the fluid is used to determine the kinematic viscosity ($kV_{standard}$) at a fixed standard temperature ($T_{standard}$), rather than the fluid temperature at the point where the viscosity of the fluid is measured. Thus, the Walter-MacCaull equation used to determine the kinematic viscosity ($kV_{standard}$) at a fixed standard temperature ($T_{standard}$) is:

$$\log_{10}(\log_{10}(kV_{standard}+0.7))=\log_{10}(\log_{10}(kV_n+0.7))-B(\log_{10}(T_{Vn})-\log_{10}(T_{standard})) \text{ or}$$

$$kV_{standard}=(kV_n+0.7)^{(Tvn/Tstandard)^{\wedge}B}-0.7.$$

Preferably, the kinematic viscosity of the fluid ($kV_{standard}$) at a standard temperature ($T_{standard}$) is continuously determined in real time to monitor the level of fluid degradation in the system 1.

According to another aspect of the invention, when the continuous fluid property measurements ($P_n$) are fluid temperature measurements ($T_n$), the fluid temperature measurements ($T_n$) may be used to update the coefficients (A and B; a and b) of the kinematic viscosity equation (e.g. Walter-MacCaull equation) and density equation that characterize the fluid. As the fluid in the system 1 degrades, the values of these coefficients (A and B; a and b) can change. Also, these coefficients may need to be updated such that the determinations of fluid viscosity adjust to fluctuations in operating conditions of the system 1. For example, the threshold for updating the coefficients may be a 5° C. change between temperature measurements ($T_n$). Then, new temperature measurements ($T_n$) and corresponding absolute viscosity determinations (aVn) may be collected at least ten times per hour for at least twelve hours to update the coefficients (A and B; a and b) of the kinematic viscosity equation (e.g. Walter-MacCaull equation) and density equation that characterize the fluid. New coefficients (A and B; a and b) of the kinematic viscosity equation (e.g. Walter-MacCaull equation) and density equation may be determined in the same manner described above. Thus, more accurate determinations of kinematic viscosity of the fluid ($kV_{standard}$) at a standard temperature ($T_{standard}$) can be achieved.

According to yet another aspect of the invention, sensors can also be incorporated in the system 1 to determine and signal laminar and turbulent flow conditions. For example, if sensors of the system 1 determined that the flow of the fluid through the system 1 was laminar, then the method of determining viscosity of the present invention would be allowed to proceed. However, if the sensors of the system 1 determined that the flow of the fluid through the system 1 were turbulent, then the viscosity determination would be paused until a laminar flow condition was detected and signaled to an appropriate data processor (not shown in FIG. 2).

According to another method, determining kinematic viscosity ($kV_{standard}$) at a standard temperature ($T_{standard}$) comprises measuring at least two properties of the fluid ($P_i$, $P_{ii}$) in the system 1 rather than one property of the fluid (P). Further, the virtual temperature ($T_V$) of the fluid is determined using the measurements of the at least two properties of the fluid (($P_{i\,n}$, $P_{ii\,n}$)).

The properties of the fluid ($P_i$, $P_{ii}$) can be any properties of the fluid that are correlated to the temperature of the fluid where the viscosity of the fluid is measured, including, but not limited to conductivity, impedance, viscosity, and another fluid temperature. In one embodiment, the properties of the fluid ($P_i$, $P_{ii}$) can be multiple fluid temperatures measured at different points in the system 1. The properties of the fluid ($P_i$, $P_{ii}$) can be measured at different points in the system 1 and can be measured by one sensor, multiple sensors, or a combination of sensors. Preferably, measurements of the fluid properties ($P_{i\,n}$, $P_{ii\,n}$) are taken continuously at least ten times per hour and for at least ten days.

Then, a virtual temperature ($T_{Vn}$) may be determined by correlating it to measurements of fluid properties ($P_{i\,n}$, $P_{ii\,n}$) in the system 1. An equation correlating the virtual temperature ($T_V$) of the fluid to properties of the fluid ($P_{i\,n}$, $P_{ii\,n}$) can be obtained by performing a regression on virtual temperature values ($T_{Vn}$) and measurements of fluid properties ($P_{i\,n}$, $P_{ii\,n}$) in the system 1. The virtual temperature values ($T_{Vn}$) of the regression may be determined as described in the embodiments above.

Once the continuous measurements of the properties of the fluid ($P_{i\,n}$, $P_{ii\,n}$) and corresponding virtual temperature values ($T_{Vn}$) of the fluid are collected, a regression may be performed on the data set to determine a relationship that correlates the measurements of the properties of the fluid ($P_{i\,n}$, $P_{ii\,n}$) to the virtual temperature values ($T_{Vn}$). The relationship that correlates the empirical data points ($P_{i\,n}$, $P_{ii\,n}$) and ($T_{Vn}$) can be any conventional mathematical relationship.

EXAMPLE

To illustrate the difficulty of determining kinematic viscosity using measured temperature values, the kinematic viscosity of a fluid ($kV_{standard}$) was calculated for a series of $kV_n$, $T_n$ pairs, with the following procedure. A sample of a fluid circulating in a continuous system was obtained, and characterized under laboratory conditions as having a kinematic viscosity @ 100° C.=18.79 cSt, a kinematic viscosity @ 40° C.=217.2 cSt, and a density @ 60° F.=0.890 g/ml. The Walther-MacCaull equation was fitted with these viscosity values to yield the A and B constants: A=8.8387 and B=−3.3937. A period of relative temperature stability was selected to obtain an approximate value to the resistance to flow of the piping from the circulation system. Using the Hagen-Poiseuille Equation: $aV=(P_1-P_2)*C/F$; at an average fluid temperature of 56.13° C., a value for $(P_1-P_2)/F$ was approximated to ~3, yielding an approximated value for the calibration coefficient (C) of ~31. Using this constant in the Hagen-Poiseuille equation, the absolute viscosity ($aV_n$) was calculated for a period of 30 days online and the kinematic viscosity ($kV_n$) was approximated by dividing the absolute viscosity ($aV_n$) by the density ($D_n$) of the fluid. The kinematic viscosities ($kV_n$) were then extrapolated to kinematic viscosities ($kV_{standard}$) at 40° C. ($T_{standard}$), using the equation:

$$kV_{standard} = (kV_n + 0.7)^{(Tn/T40)^B} - 0.7 = (kV_n + 0.7)^{(Tn/313.15)^B} - 0.7$$

Figure 3:
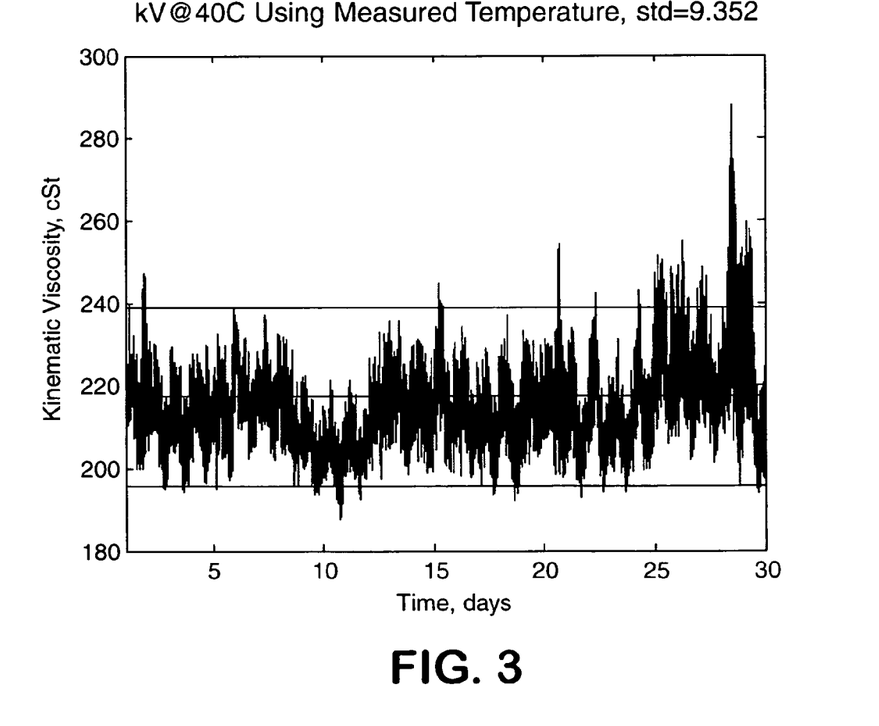
FIG. 3 depicts a graph of kinematic viscosity at 40° C. over time, calculated using measured temperature.

As shown by the graph in FIG. 3, this procedure yielded an unsatisfactory standard deviation of 9.34 cSt, but reasonable considering the difficulties with temperature measurement ($T_n$) in addition to compounding of all measurement errors (e.g., flow, pressure, temperature).

The virtual temperature ($T_{Vn}$) was then used to estimate the kinematic viscosity ($kV_{standard}$) at 40° C. ($T_{standard}$) over the entire period of 30 days, in a way similar to the procedure above.

First, a virtual temperature ($T_V$) function was obtained by back-calculating a series of virtual temperature values ($T_{Vn}$) from a series of measured absolute viscosity values ($aV_n$), such that the virtual temperature values ($T_{Vn}$) represented those temperatures that would yield the measured absolute viscosity values ($aV_n$):

$$\log_{10} T_{Vn} = [A - \log_{10}(\log_{10}(D_n(T_n)*aV_n + 0.7))]/B$$

Then, the function $T_{Vn} = a + b*T_n$ was obtained through a simple linear regression of the virtual temperature values ($T_{Vn}$) and measured temperature values ($T_n$).

Figure 4:
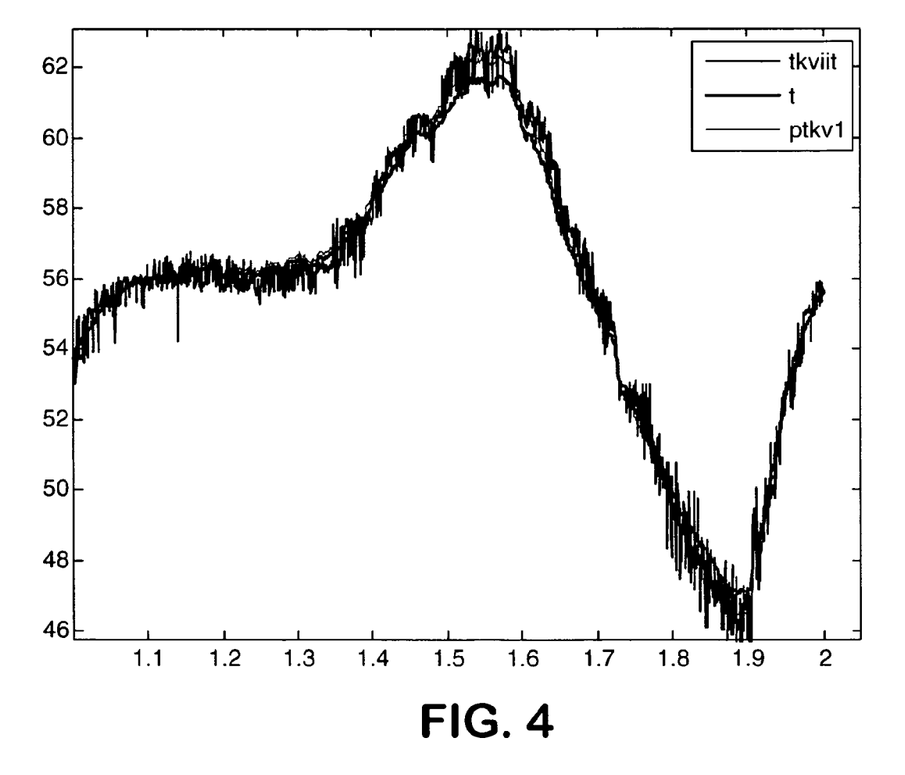
FIG. 4 depicts a graph of measured temperatures, back calculated virtual temperatures, and predicted virtual temperatures over time.

Then, the linear function, $T_{Vn} = a + b*T_n$, was used to estimate the kinematic viscosity ($kV_{standard}$) @ 40° C. ($T_{standard}$). A period of one day (between day=1 and day=2) was used to estimate the virtual temperature equation coefficients covering a range of temperatures (e.g., 46° C.-62° C.) sufficient to generate the a and b constants for the regression. FIG. 4 shows the actual measured temperatures ($T_n$), the virtual temperature values ($T_{Vn}$) back calculated from the kinematic viscosity determinations ($kV_n$), and predicted virtual temperature values ($T_{Vn}$) obtained using the virtual temperature function defined above. As shown, the predicted virtual temperature values ($T_{Vn}$) followed the back-calculated virtual temperature values ($T_{Vn}$) much better than the actual measured temperatures ($T_n$). For these particular examples, the coefficients for the $T_{Vn} = a + b*T_n$ equation were: a=−4.4129; b=1.0804.

Figure 5:
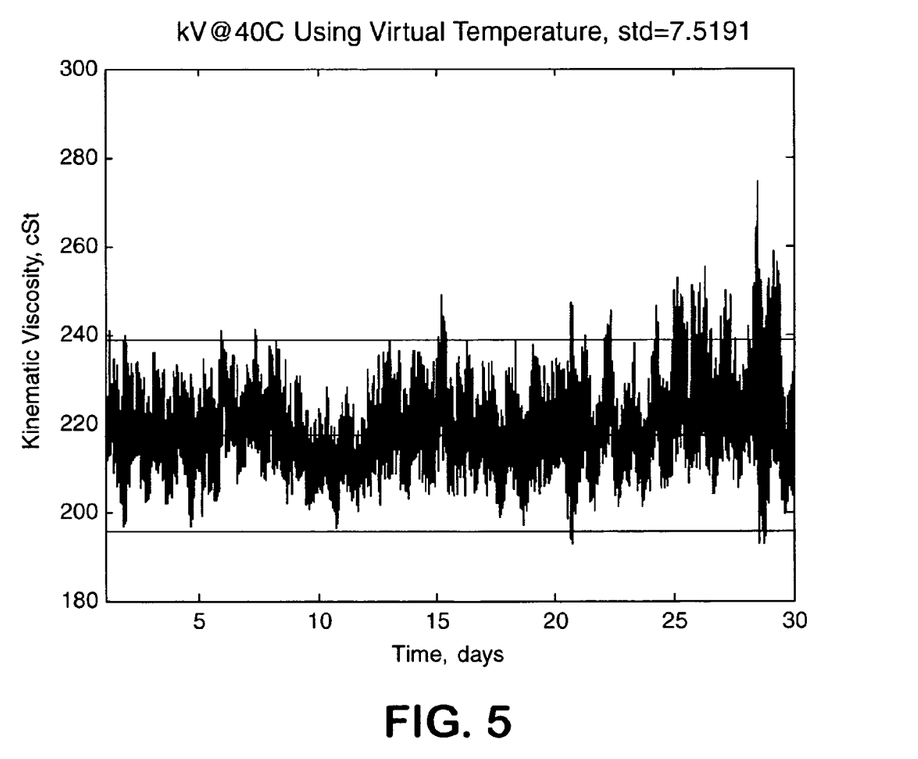
FIG. 5 depicts a graph of kinematic viscosity at 40° C. over time, calculated using virtual temperature.

As shown by the graph in FIG. 5, this estimate of the virtual viscosity temperature resulted in a 20% improvement on the standard deviation of the predictions, and a reduction in bias over the 30 day period (std=9.35 cSt; bias=−3.15 cSt with measured temperature; std=7.52 cSt, bias=0.81 cSt with virtual temperature).

What is claimed is:

1. A method comprising:
    flowing fluid through a system, the system comprising a flow meter and at least one additional sensor for measuring at least one additional property
    determining an absolute viscosity (aV) of the fluid at a section A in the system using the flowmeter;
    measuring a property of the fluid (P) in the system using at least one sensor for measuring at least one additional property;
    determining a virtual temperature ($T_V$) of the fluid at section A using the measured property of the fluid (F) with a relationship that correlates the property of the fluid (F) with the virtual temperature ($T_V$) of the fluid at section A;
    estimating a kinematic viscosity (kV) of the fluid from the absolute viscosity (aV) of the fluid at section A; and
    extrapolating the kinematic viscosity ($kV_{standard}$) of the fluid at a standard temperature ($T_{standard}$) using the kinematic viscosity (kV) of the fluid, the virtual temperature ($T_V$) of the fluid, and a relationship that correlates the temperature of the fluid with the kinematic-viscosity of the fluid to determine on-line the kinematic viscosity of the fluid at any temperature.

2. The method of claim 1 wherein determining absolute viscosity (aV) comprises:
    determining pressure ($P_1$) of the fluid at a first location in a system;
    determining pressure ($P_2$) of the fluid at a second location in the system downstream from the first location;
    determining flow rate (F) of the fluid through the system;
    determining calibration coefficient (C) of the system; and
    determining aV using the Hagen-Poiseuille law.

3. The method of claim 2 wherein the Hagen-Poiseuille law is represented by the equation: $aV = (P_1 - P_2)*C/F$.

4. The method of claim 2 wherein
    determining pressure ($P_1$) comprises taking pressure measurements of the fluid at said first location in the system over a period having a range of fluid temperatures and obtaining an average pressure measurement;
    determining pressure ($P_2$) comprises taking pressure measurements of the fluid at said second location in the system over said period and obtaining an average pressure measurement;
    determining flow rate (F) comprises by taking flow rate measurements of the fluid through the system over said period and obtaining an average flow rate measurement; and
    determining calibration coefficient (C) comprises:
        measuring the temperature (T) of the fluid in the system;
        identifying an absolute viscosity ($aV_n$) of the fluid corresponding to the measured temperature (T) of the fluid using a relationship that correlates the absolute viscosity of the fluid with the temperature of the fluid; and
        determining C using the relationship: $C = aV_n * F/(P_1 - P_2)$.

5. The method of claim 1 wherein determining the virtual temperature ($T_V$) of the fluid at section A comprises:
    characterizing a relationship that correlates the temperature and said property of the fluid under controlled laboratory conditions;
    taking at least three measurements ($P_n$) of said property of the fluid in the system, spanning an operational fluid temperature range for the system;
    estimating virtual temperature values ($T_{Vn}$) of the fluid at section A corresponding to the measurements ($P_n$) of said property of the fluid in the system by using the characterized relationship that correlates the temperature and said property of the fluid;
    characterizing a relationship that correlates said property of the fluid and the virtual temperature of the fluid using the at least three property measurements ($P_n$) and corresponding virtual temperature values ($T_{Vn}$); and
    determining the virtual temperature ($T_V$) of the fluid at section A of the system using the measured property of the fluid (P) and the characterized relationship that correlates said property of the fluid and the virtual temperature of the fluid.

6. The method of claim 1 wherein determining the virtual temperature ($T_V$) of the fluid at section A comprises:
    characterizing a relationship that correlates the temperature and said properly of the fluid under controlled laboratory conditions;
    taking at least three measurements ($P_n$) of said property of the fluid in the system, spanning an operational fluid temperature range for the system;

estimating virtual temperature values ($T_{Vn}$) of the fluid at section A corresponding to the measurements ($P_n$) of said property of the fluid in the system by using the characterized relationship between said property of the fluid and the temperature of the fluid;

estimating linear regression coefficients a and b for the relationship: $T_{Vn}=a+b*P_n$, that best fit the at least three corresponding property measurements ($P_n$) and temperature values ($T_{Vn}$); and determining the virtual temperature ($T_V$) of the fluid at section A of the system from the relationship: $T_V=a+b*P$.

7. The methods of claim 5 or 6 wherein said property of the fluid (P) in the system is one of a group of properties correlated to the temperature of the fluid, including, but not limited to conductivity, impedance, and viscosity.

8. The methods of claim 5 or 6 wherein said property of the fluid (P) in the system comprises a mathematically functional combination of two or more properties from a group of properties correlated to the temperature of the fluid, including but not limited to conductivity, impedance, viscosity, and temperature.

9. The method of claim 1 wherein the relationship that correlates the temperature of the fluid with the kinematic-viscosity of the fluid is the Walther-MacCaull equation.

10. The method of claim 1 wherein estimating the kinematic viscosity (kV) comprises:
estimating a density (D) of the fluid at section A using the virtual temperature ($T_V$) of the fluid at section A and a relationship that correlates the temperature of the fluid with the density of the fluid; and
determining kV using the absolute viscosity (aV) of the fluid, the density (D) of the fluid, and a relationship that correlates the absolute viscosity and density of the fluid with the kinematic viscosity of the fluid.

11. The method of claim 1 wherein estimating the kinematic viscosity (kV) comprises:
estimating a density (D) of the fluid at section A using the virtual temperature ($T_V$) of the fluid at section A and a characterized relationship that correlates density and temperature for the fluid; and
determining kV from the relationship: $kV=aV/D$.

12. The method of claim 1 wherein the additional properties are chosen from the group consisting of conductivity, impedance viscosity, fluid temperature viscosity, pressure, density and any combination thereof.

13. The method of claim 1 wherein the sensor is selected from the group consisting of thermocouple, pressure transducer, density sensor, and any combination thereof.

14. An on-line method for estimating kinematic viscosity ($kV_{standard}$) of a fluid flowing through a system, comprising:
determining an absolute viscosity (aV) of the fluid at a section A in the system using a flowmeter;
measuring a temperature (T) of the fluid in the system;
determining a virtual temperature ($T_V$) of the fluid at section A using the measured temperature (T) with a relationship that correlates the temperature ($T_B$) of the fluid at point B with the virtual temperature ($T_V$) of the fluid at section A;
estimating the kinematic viscosity (kV) of the fluid from the absolute viscosity (aV) of the fluid at section A; and
extrapolating the kinematic viscosity ($kV_{standard}$) of the fluid at a standard temperature ($T_{standard}$) using the kinematic viscosity (kV) of the fluid, the virtual temperature ($T_V$) of the fluid, and a relationship that correlates the temperature of the fluid with the kinematic-viscosity of the fluid.

15. The method of claim 14 wherein determining the virtual temperature ($T_V$) of the fluid at section A comprises:
characterizing a relationship that correlates the kinematic-viscosity and temperature of the fluid and a relationship that correlates the density and temperature of the fluid by measuring at least two corresponding sets of kinematic viscosity, density, and temperature values under controlled laboratory conditions, and using equations for kinematic-viscosity or density extrapolation;
measuring at least three corresponding pairs of absolute viscosity values ($aV_n$) of the fluid at section A in the system and temperature values ($T_n$) of the fluid in the system, spanning an operational temperature range for the system;
estimating kinematic viscosity ($kV_n$) values corresponding to said absolute viscosity ($aV_n$) values of the fluid at section A in the system by
approximating corresponding density ($D_n$) values of the fluid using the measured temperature values ($T_n$) of the fluid in the system and the characterized density/temperature relationship of the fluid; and
estimating the kinematic viscosity ($kV_n$) values from the relationship: $kV_n=aV_n/D_n$;
estimating corresponding virtual temperature ($T_{Vn}$) values of the fluid at section A from the estimated kinematic viscosity ($kV_n$) values by using the characterized kinematic-viscosity/temperature relationship of the fluid;
estimating linear regression coefficients a and b for the relationship: $T_{Vn}=a+b*T_n$, that best fit the at least three corresponding sets of temperature values ($T_{Vn}$) and ($T_n$); and
determining the virtual temperature ($T_V$) of the fluid at section A of the system from the relationship: $T_V=a+b*T$.

16. The method of claim 14 wherein determining the virtual temperature ($T_V$) of the fluid at section A of the system comprises:
characterizing a relationship that correlates the kinematic-viscosity and temperature of the fluid and a relationship that correlates density and temperature of the fluid by measuring at least two corresponding sets of kinematic viscosity, density, and temperature values under controlled laboratory conditions, and using equations for kinematic-viscosity or density extrapolation;
measuring at least three corresponding sets of absolute viscosity values ($aV_n$) of the fluid at section A in the system, temperature values ($T_n$) of the fluid in the system, and values of at least one other property ($P_n$) of the fluid iii the system, spanning a practical temperature range for the system;
estimating kinematic viscosity ($kV_n$) values corresponding to said absolute viscosity ($aV_n$) values of the fluid at section A in the system by
approximating corresponding density values ($D_n$) of the fluid using the temperature values ($T_n$) of the fluid in the system and the characterized relationship that correlates the density and temperature of the fluid; and
estimating the kinematic viscosity ($kV_n$) values from the relationship: $kV_n{-}aV_n/D_n$;
estimating virtual temperature ($T_{Vn}$) values of the fluid at section A from the estimated kinematic viscosity ($kV_n$) values by using the characterized kinematic-viscosity/temperature relationship of the fluid;
estimating the linear regression coefficients a and b for the relationship: $T_{Vn}=a+b*P_n$, that best fit the at least three corresponding sets of temperature values ($T_{Vn}$) and properly values ($P_n$);

measuring said at least one other property of the fluid (F) in the system; and determining the virtual temperature ($T_V$) of the fluid at section A of the system from the relationship: $T_V = a + b*P$.

17. The method of claim 16 wherein said at least one other property of the fluid is at least one of a group of properties correlated to the temperature of the fluid, including but not limited to conductivity, impedance, and viscosity.

18. The method of claim 16 wherein said at least one other property of the fluid comprises a mathematically functional combination of two or more properties from a group of properties correlated to the temperature of the fluid, including but not limited to conductivity, impedance, viscosity, and temperature.

19. The method of claim 14 wherein the relationship that correlates the kinematic-viscosity of the fluid with the temperature of the fluid is a Walther-MacCaull equation.

20. The method of claim 14 wherein estimating the kinematic viscosity (kV) comprises:

estimating a density (D) of the fluid at section A using the virtual temperature ($T_V$) of the fluid at section A and a density/temperature relationship for the fluid; and determining kV from a relationship using the absolute viscosity (aV) of the fluid, the density (D) of the fluid, and a relationship between the kinematic viscosity, absolute viscosity, and density of the fluid.

21. The method of claim 14 wherein estimating the kinematic viscosity (kV) comprises:

estimating a density (D) of the fluid at section A using the virtual temperature ($T_V$) of the fluid at section A and a calibrated density/temperature chart for the fluid; and determining kV from the relationship: kV=aV/D.

22. A method comprising:

Flowing fluid through a system, the system comprising a flowmeter, and at least two additional sensors for measuring at least two additional properties determining an absolute viscosity (aV) of the fluid at a section A in the system using the flowmeter;

measuring at least two properties ($P_i$, $P_{ii}$) of the fluid at different points in the system using at least two sensors for measuring at least two additional properties;

determining a virtual temperature ($T_V$) of the fluid at section A using the measured at least two properties ($P_i$, $P_{ii}$) of the fluid with a relationship that correlates the at least two properties ($P_i$, $P_{ii}$) of the fluid with the virtual temperature ($T_V$) of the fluid at section A;

estimating the kinematic viscosity (kV) of the fluid from the absolute viscosity (aV) of the fluid at section A; and extrapolating the kinematic viscosity ($kV_{standard}$) of the fluid at a standard temperature ($T_{standard}$) using the kinematic viscosity (kV) of the fluid, the virtual temperature ($T_V$) of the fluid, and a relationship that correlates the temperature of the fluid with the kinematic-viscosity of the fluid to determine on-line the kinematic viscosity of the fluid at any temperature.

* * * * *